(12) United States Patent
Desinger et al.

(10) Patent No.: US 8,092,449 B2
(45) Date of Patent: *Jan. 10, 2012

(54) SURGICAL PROBE (75) Inventors: Kai Desinger, Berlin (DE); Markus Fay, Berlin (DE); Andre Roggan, Berlin (DE)

(73) Assignee: Celon AG (DE)

( * ) Notice: Subject to any disclaimer, the term of this patent is extended or adjusted under 35 U.S.C. 154(b) by 114 days.

This patent is subject to a terminal disclaimer.

(21) Appl. No.: 10/564,322

(22) PCT Filed: Jul. 8, 2004

(86) PCT No.: PCT/EP2004/007519
§ 371 (c)(1),
(2), (4) Date: Jun. 26, 2006

(87) PCT Pub. No.: WO2005/006998
PCT Pub. Date: Jan. 27, 2005

(65) Prior Publication Data
US 2006/0271031 A1    Nov. 30, 2006

(30) Foreign Application Priority Data
Jul. 11, 2003  (DE) .................................. 103 32 564

(51) Int. Cl.
*A61B 18/18* (2006.01)
(52) U.S. Cl. ............................................. 606/41; 606/50
(58) Field of Classification Search .................... 606/41, 606/46–56; 600/459
See application file for complete search history.

(56) References Cited

U.S. PATENT DOCUMENTS

| | | | |
|---|---|---|---|
| 3,568,660 A * | 3/1971 | Crites et al. | 607/122 |
| 4,043,342 A | 8/1977 | Morrison | |
| 4,449,528 A * | 5/1984 | Auth et al. | 606/31 |
| 4,660,571 A | 4/1987 | Hess et al. | |
| 4,674,499 A * | 6/1987 | Pao | 606/50 |
| 4,688,569 A * | 8/1987 | Rabinowitz | 606/42 |
| 4,765,331 A | 8/1988 | Petruzzi et al. | |
| 4,832,048 A | 5/1989 | Cohen | |
| 4,907,589 A * | 3/1990 | Cosman | 606/34 |
| 5,009,656 A | 4/1991 | Reimels | |
| 5,123,903 A | 6/1992 | Quaid et al. | |
| 5,167,619 A | 12/1992 | Wuchinich | |
| 5,221,281 A * | 6/1993 | Klicek | 606/45 |
| 5,267,994 A * | 12/1993 | Gentelia et al. | 606/15 |
| 5,281,215 A | 1/1994 | Milder | |

(Continued)

FOREIGN PATENT DOCUMENTS
DE        38 34 230      10/1988
(Continued)

OTHER PUBLICATIONS
PCT International Search Report.
(Continued)

*Primary Examiner* — Linda Dvorak
*Assistant Examiner* — Amanda Scott
(74) *Attorney, Agent, or Firm* — Ostrolenk Faber LLP (57) ABSTRACT The invention concerns a surgical probe having electrodes for use in tissue ablation or coagulation. The probe has hollow spaces therein for delivering a cooling fluid to the probe. The probe has a handle and shaft and two axially-spaced electrodes on the surface of the shaft, separated from each other by an insulator.

10 Claims, 5 Drawing Sheets

U.S. PATENT DOCUMENTS

| | | | |
|---|---|---|---|
| 5,330,470 A | | 7/1994 | Hagen |
| 5,403,311 A | * | 4/1995 | Abele et al. ............... 606/49 |
| 5,458,597 A | * | 10/1995 | Edwards et al. ............ 606/41 |
| 5,462,545 A | | 10/1995 | Wang et al. |
| 5,520,684 A | | 5/1996 | Imran |
| 5,728,130 A | | 3/1998 | Ishikawa et al. |
| 5,807,395 A | * | 9/1998 | Mulier et al. ............... 606/41 |
| 5,833,689 A | | 11/1998 | Long |
| 5,913,854 A | * | 6/1999 | Maguire et al. ............ 606/41 |
| 5,913,856 A | | 6/1999 | Chia et al. |
| 6,004,319 A | | 12/1999 | Goble et al. |
| 6,036,687 A | | 3/2000 | Laufer et al. |
| 6,142,994 A | * | 11/2000 | Swanson et al. ........... 606/41 |
| 6,146,379 A | | 11/2000 | Fleischman et al. |
| 6,210,406 B1 | * | 4/2001 | Webster ...................... 606/41 |
| 6,358,249 B1 | | 3/2002 | Chen et al. |
| 6,379,349 B1 | * | 4/2002 | Muller et al. ............... 606/41 |
| 6,529,760 B2 | * | 3/2003 | Pantages et al. ........... 600/407 |
| 6,605,085 B1 | * | 8/2003 | Edwards ..................... 606/41 |
| 6,723,094 B1 | * | 4/2004 | Desinger .................... 606/50 |
| 6,757,565 B2 | * | 6/2004 | Sharkey et al. ............ 607/99 |
| 2002/0077624 A1 | | 6/2002 | Lehmann |
| 2002/0120258 A1 | * | 8/2002 | Lalonde ..................... 606/23 |
| 2004/0167517 A1 | * | 8/2004 | Desinger et al. ........... 606/50 |

FOREIGN PATENT DOCUMENTS

| | | |
|---|---|---|
| DE | 39 30 451 A1 | 9/1991 |
| DE | 39 30 451 A1 | 3/1992 |
| DE | 197 39 699 | 9/1997 |
| DE | 101 28 701 | 6/2001 |
| EP | 0 543 122 | 10/1992 |
| EP | 0 651 974 A | 5/1995 |
| EP | 0 856 292 | 8/1998 |
| JP | 11-504539 | 4/1999 |
| JP | 2002-507924 | 3/2002 |
| JP | 2002-532186 | 10/2002 |
| WO | WO 81/03272 | 5/1981 |
| WO | WO 95/10320 | 4/1995 |
| WO | WO 95/17855 | 7/1995 |
| WO | WO 96/18349 | 6/1996 |
| WO | WO 96/34569 | 11/1996 |
| WO | WO 96/34569 | 11/1996 |
| WO | WO 97/00647 | 1/1997 |
| WO | PCT/US96/13285 | 2/1997 |
| WO | WO 97/17009 | 5/1997 |
| WO | WO 98/19613 | 5/1998 |
| WO | WO 99/01074 | 1/1999 |
| WO | WO 99/11186 | 3/1999 |
| WO | WO 99/15120 | 4/1999 |
| WO | PCT/EP99/10079 | 6/2000 |
| WO | WO 02/098312 A3 | 12/2002 |

OTHER PUBLICATIONS

German Translation of Japanese Office Action issued Aug. 11, 2010 in connection with corresponding Japanese Patent Application No. 2006-519836.

* cited by examiner

SURGICAL PROBE

This application is a national stage filing of and claims priority to PCT/EP2004/07519, filed Jul. 8, 2004 and claims priority to German Patent Application 103 32 564.6 dated Jul. 11, 2003, and is a continuation-in-part of and claims priority to U.S. Ser. No. 10/806,867, filed Mar. 23, 2004, which in turn is a divisional of and claims priority to U.S. Pat. No. 6,723,094, issued Apr. 20, 2004 which in turn claims priority to PCT/EP99/10079, filed Dec. 17, 1999 which in turn claims priority to DE 198 58 599.3, filed Dec. 18, 1998.

FIELD OF THE INVENTION

The invention concerns a surgical probe comprising a handle and a shaft which is connected to the handle and has at least two axially mutually spaced electrodes. One electrode which is closer to the handle forms a proximal electrode and the other electrode which is further away from the handle forms a distal electrode. The electrodes respectively form an electrically conducting outside surface of the shaft and are axially separated from each other by an insulator. The outside diameter of the two electrodes and the outside diameter of the insulator are approximately the same. The shaft also has a fluid passage which extends in the interior of the shaft from the handle into the distal electrode so that proximal and distal electrodes are to be temperature-controlled by a fluid, for example they are to be cooled or pre-heated. In accordance with the main area of use reference is usually made hereinafter to cooling fluid or liquid. In particular situations of use that also means a fluid for temperature-control or also heating of the probe.

BACKGROUND OF THE INVENTION

Surgical probes of that kind are basically known and serve for example for tissue ablation or coagulation. For that purpose the shaft with the two electrodes is inserted into body tissue. For example a high-frequency ac voltage is applied to the two electrodes, and that causes an alternating current in the body tissue surrounding the shaft and causes it to be heated. The high-frequency current and the electrode geometry are so selected in that case that the heating of the body tissue which occurs as a consequence of the high-frequency current results in cell death and thus tissue sclerosis. It is possible in that way to treat for example tumors.

In order better to distribute the energy which is introduced into the body tissue and to prevent for example body tissue in the proximity of the electrodes from almost burning while scarcely any heat is still being produced at just a short distance from the electrodes, it is known for the electrodes to be cooled during delivery of the high-frequency current or heated to provide for ablation of the puncture passage. As cooling is particularly effective where the electrical field strengths are particularly high, it is possible in that way for heating of the body tissue to be more uniformly distributed to a greater volume.

The desire to be able to provide for temperature control of the electrodes involves further problems in regard to the structure of the shaft of the surgical probe. On the one hand the cooling liquid can be conducting (for example physiological saline solution) so that the cooling liquid can result in short-circuits between the two electrodes in the interior of the shaft. On the other hand the fluid passage for the cooling fluid requires a hollow electrode structure so that, with the shaft being of a small diameter which is also desired at the same time, it is only with difficulty that all demands in terms of mechanical strength and sealing integrity of the shaft can be met. That is especially the case insofar as the shaft of the surgical probe is usually inserted into the body tissue for treating same.

The known approaches for equally well satisfying all demands on a fluid-temperature-controlled surgical probe for interstitial thermotherapy are for the most part not totally satisfactory. Therefore the object of the invention is to provide a surgical probe which has good cooling properties, which has good electrical properties, which enjoys high mechanical strength and which in addition affords sealing integrity at high fluid pressures.

SUMMARY OF THE INVENTION

According to the invention that object is obtained by a surgical probe of the kind set forth in the opening part of this specification, in which the shaft has a distally closed hollow body which is connected to the handle, forms the distal electrode and carries the insulator and the proximal electrode. That shaft also has an insulating layer which is arranged in the radial direction between the hollow body and the proximal electrode.

The hollow body is preferably of an integral nature. A particularly preferred, integral hollow body is produced by welding a first tubular component to a second component forming the closed distal end.

More specifically it has been found that it is possible for an electrical insulating layer which basically adversely affects cooling of the proximal electrode to be so designed that heat conduction is in practice not adversely affected by the insulating layer.

In order to adversely affect cooling of the proximal electrode to the least possible extent, the insulating layer is preferably only a few micrometers thick, for example between 1 and 10 μm.

The insulating layer is preferably arranged both between the hollow body and the proximal electrode and also between the hollow body and the insulator. In an alternative configuration which is particularly preferred in particular also from manufacturing points of view, the insulating layer is formed by shrink tube.

The insulator and preferably also the proximal electrode are preferably each in the form of a tube of a substantially uniform wall thickness so that the insulator and the proximal electrode are to be pushed on to the hollow body and the shrink tube which is shrunk on to the hollow body.

The hollow body preferably has a portion of an enlarged outside diameter where the hollow body forms the distal electrode. Proximally of that portion the hollow body is preferably of a smaller diameter. The shrink tube can be pushed on to and shrunk on that portion of the hollow body of smaller diameter. Then the insulator and the proximal electrode can be pushed on to that portion. The diameters of the hollow body, the insulator and the proximal electrode are preferably such that the inside diameter of the insulator and the proximal electrode permit them to be pushed on to the shrink tube. In addition the outside diameter of the portion of the hollow body of enlarged diameter, which forms the distal electrode, as well as the outside diameters of the insulator and the proximal electrode are equal to each other as much as possible, thus affording a shaft with an outside diameter which is equal throughout as much as possible. Approximately equal means in this case that the outside diameters of the distal electrode, the insulator and proximal electrodes should correspond to the limits of manufacturing accuracies. For such an embodiment the proximal electrode is preferably in the form of a metal tube with outside and inside diameters which are substantially equal over its length, that is to say also of substantially equal wall thickness. The expression 'substantially equal' does not exclude bevels and screwthreads at the proximal electrode, any more than manufacturing inaccuracies.

In an alternative configuration the outside diameter of the proximal electrode decreases continuously from the handle in the direction of the distal end of the shaft, thus affording a for example conically shaped proximal electrode.

The hollow body is preferably closed at its distal end so that no fluid can issue from the fluid passage in the region of the shaft. The fluid passage in the interior of the hollow body preferably extends to the closed end of the hollow body and in a particularly preferred variant is of a diameter which is equal throughout. The fluid passage can be easily produced in that way.

The surgical probe also preferably has a hose in the interior of the fluid passage, which has a mouth opening in the proximity of the closed end of the fluid passage and which is so arranged and connected that a cooling fluid is to be passed through the hose into the proximity of the distal end of the fluid passage, there issues from the mouth opening of the hose and can flow back between the hose and the wall of the fluid passage to the proximal end of the shaft.

For that purpose the hose is of an outside diameter which is smaller than the inside diameter of the fluid passage. In that way it is possible to easily produce a feed for the cooling fluid to the distal end of the fluid passage by inserting a suitable hose.

At its distal end the shaft of the surgical probe is preferably shaped to a point on the outside in order to permit easy insertion of the shaft into body tissue.

At its proximal end the shaft is connected to the handle and is there preferably partially embedded in sealing material in such a way that the tube forming the proximal electrode, at the proximal end thereof, is completely embedded in the sealing material while the proximal end of the hollow body projects from the sealing material. In that case the proximal electrode is preferably electrically contacted within the sealing material, that is to say connected to an electric line, by means of which the proximal electrode can be connected to a high frequency generator. Short-circuits between the proximal electrode and the hollow body can be effectively prevented by means of the sealing material even when an electrically conducting cooling fluid is introduced into the shaft by way of the handle of the surgical probe.

The proximal end of the hollow body preferably projects beyond the proximal end of the proximal electrode and thus extends further into the handle so that the hollow body and therewith also the distal electrode can be electrically contacted in the proximity of the proximal end of the hollow body.

BRIEF DESCRIPTION OF THE FIGURES

The invention will now be described in greater detail by means of an embodiment by way of example illustrated in the Figures in which.

DETAILED DESCRIPTION OF PREFERRED EMBODIMENT(S)

Figure 1:
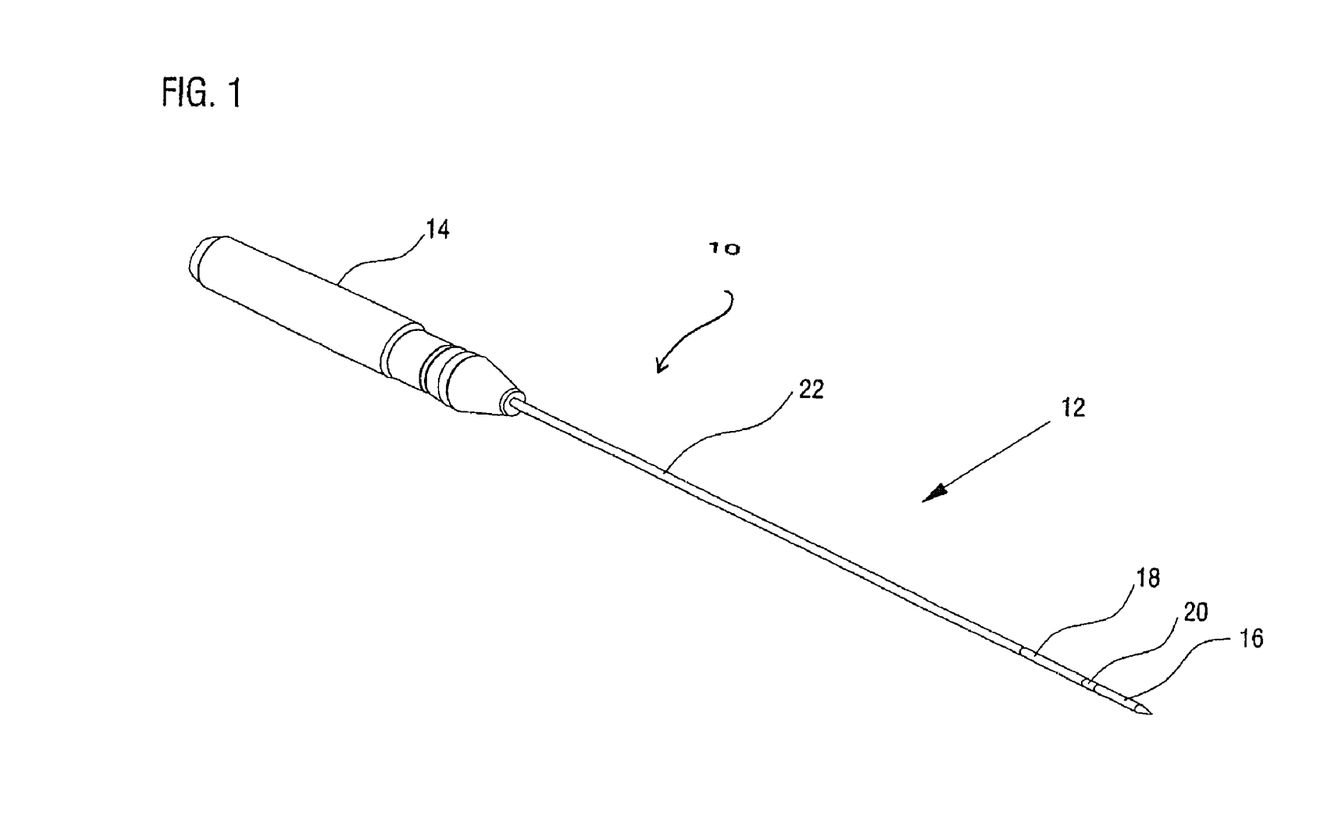
FIG. 1 shows a surgical probe according to the invention with handle and shaft.

The surgical probe 10 shown in FIG. 1 has an elongate shaft 12 which in its proximal end is connected to a handle 14. Provided at the distal end of the shaft 12 are two electrodes 16 and 18, namely a distal tip electrode 16 and a proximal electrode 18. An insulator 20 is arranged between the two electrodes. The electrodes 16 and 18 and the insulator 20 are of approximately the same outside diameter. Also provided in the proximal direction is an outer insulating layer 22 which provides that the effective electrode surface area of the proximal electrode 18 is of a similar size to the effective electrode surface area of the distal electrode 16.

In a preferred variant the proximal electrode surface area is about 10% greater than the distal electrode surface area in order to compensate for adverse cooling effects in respect of the proximal electrode as a consequence of the insulating layer.

Figure 2:
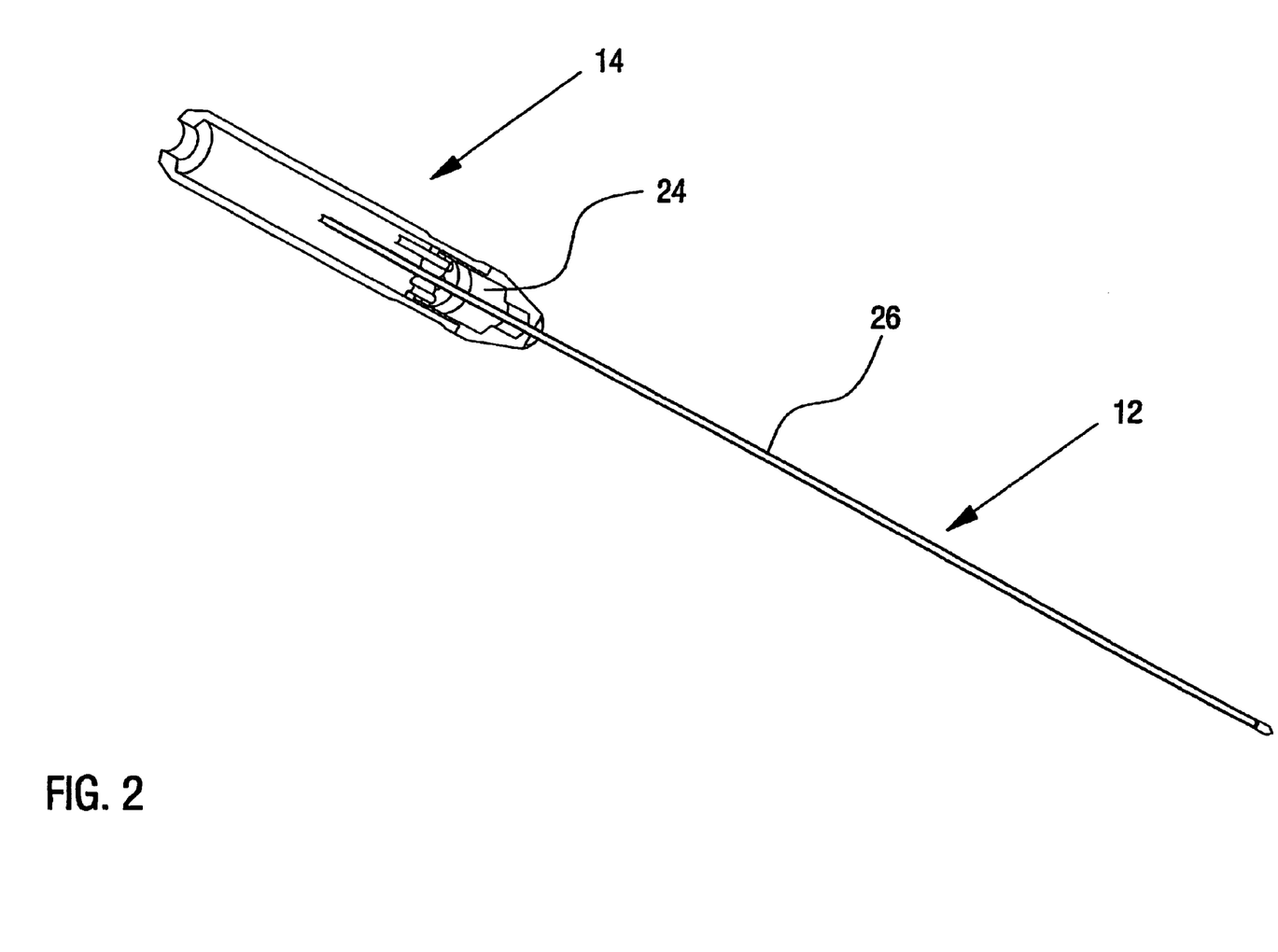
FIG. 2 shows a view in longitudinal section of the surgical probe of FIG. 1.

FIG. 2 shows a view in longitudinal section of the surgical probe 10 from FIG. 1. It will be seen that the handle 14 has a cavity 24 and in addition the shaft 12 is hollow in the interior over the major part of its length. The cavity forms a fluid passage 26 which is in fluid communication with the cavity 24.

Figure 4:
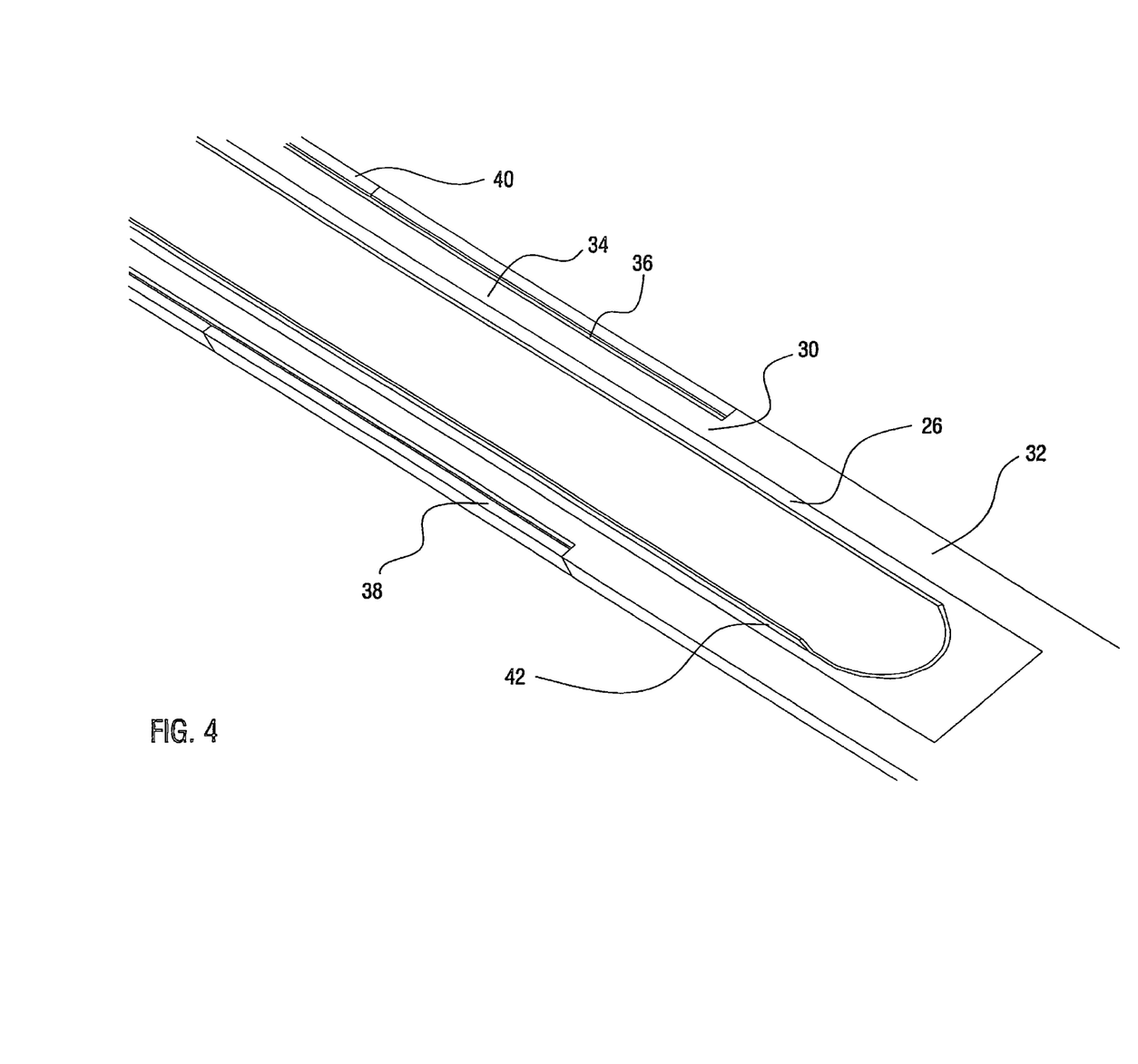
FIG. 4 shows a portion from FIG. 3 on a still further enlarged scale.

The enlarged view shown in FIG. 4 in longitudinal section of the distal end of the shaft 12 shows in detail the structure of the shaft 12: component parts of the shaft 12 are an elongate hollow body 30 with a cavity in its interior which serves as the fluid passage 26 in itself, a distal end 32 of enlarged diameter and a proximal portion 34 of smaller outside diameter; as well as an inner insulating layer 36, an insulator 38 and a metal tube 40 forming inter alia the proximal electrode. At its proximal end the metal tube 40 carries the outer insulating layer 22.

The outer surface of the distal portion 32 of the hollow body 30 forms the distal tip electrode 16.

The inner insulating layer 36 on the proximal portion 34 is formed by a shrink tube which is pushed externally on to the proximal portion 34 and which is of a wall thickness of between about 5 and 10 μm. That wall thickness affords on the one hand good electrical dielectric strength and on the other hand heat conduction which is always still good between the proximal portion 34 of the hollow body 30 and the metal tube 40.

The insulator 38 and the metal tube 40 are pushed externally on to the shrink tube 36 in such a way that the insulator 38 is arranged in the longitudinal direction between the distal portion 32 of the hollow body 30 and the metal tube 40. The insulator 38 comprises for example a thin, heat-stable plastic tube, for example of PTFE or PEEK.

The outer insulating layer 22 which is applied externally to the metal tube 40 is also formed by shrink tube. The outside surface of the metal tube 40, which is bare between the insulator 38 and the outer insulating layer 22, forms the proximal electrode 18.

An electrical connection of the distal electrode 16 to an electrical connection in the handle 14 is afforded by way of the proximal portion 34 of the hollow body 30. The hollow body 30 comprises metal.

The proximal electrode 18 is electrically connected by way of the metal tube 40 to an electrical connection in the interior of the handle 14.

Arranged in the fluid passage 26 in the interior of the hollow body 30 is a plastic hose 42, through which a cooling fluid can be passed into the proximity of the distal end of the fluid passage 26. The cooling fluid then flows back to the handle 14 on the outside of the plastic hose 42 between the plastic hose 42 and the inside wall of the fluid passage 26 in the interior of the hollow body 30.

The fluid passage 26 is formed by a bore in the interior of the hollow body 30 which for reasons relating to production engineering is preferably of the same diameter throughout.

Figure 3:
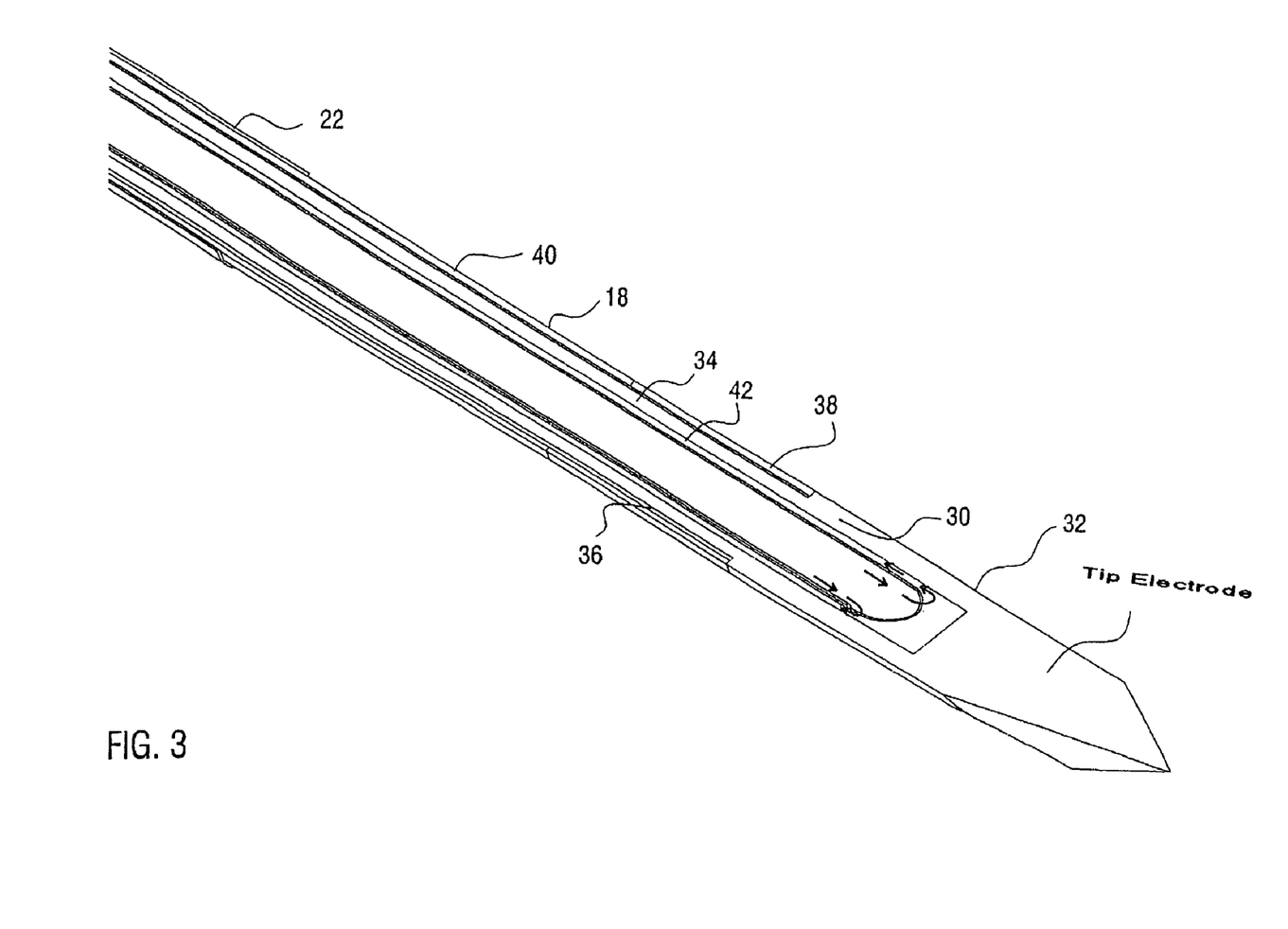
FIG. 3 shows a view in longitudinal section on an enlarged scale of the distal end of the shaft of the surgical probe of FIGS. 1 and 2.

The portion of the longitudinal section from FIG. 3 shown in FIG. 4 on an enlarged scale illustrates in even greater detail the relative arrangement of the hollow body 30 with distal portion 32 and proximal portion 34 as well as fluid passages 26 therein relative to the plastic hose 42 on the one hand and the inner insulating layer 36, the insulator 38 and the metal tube 40.

Figure 5:
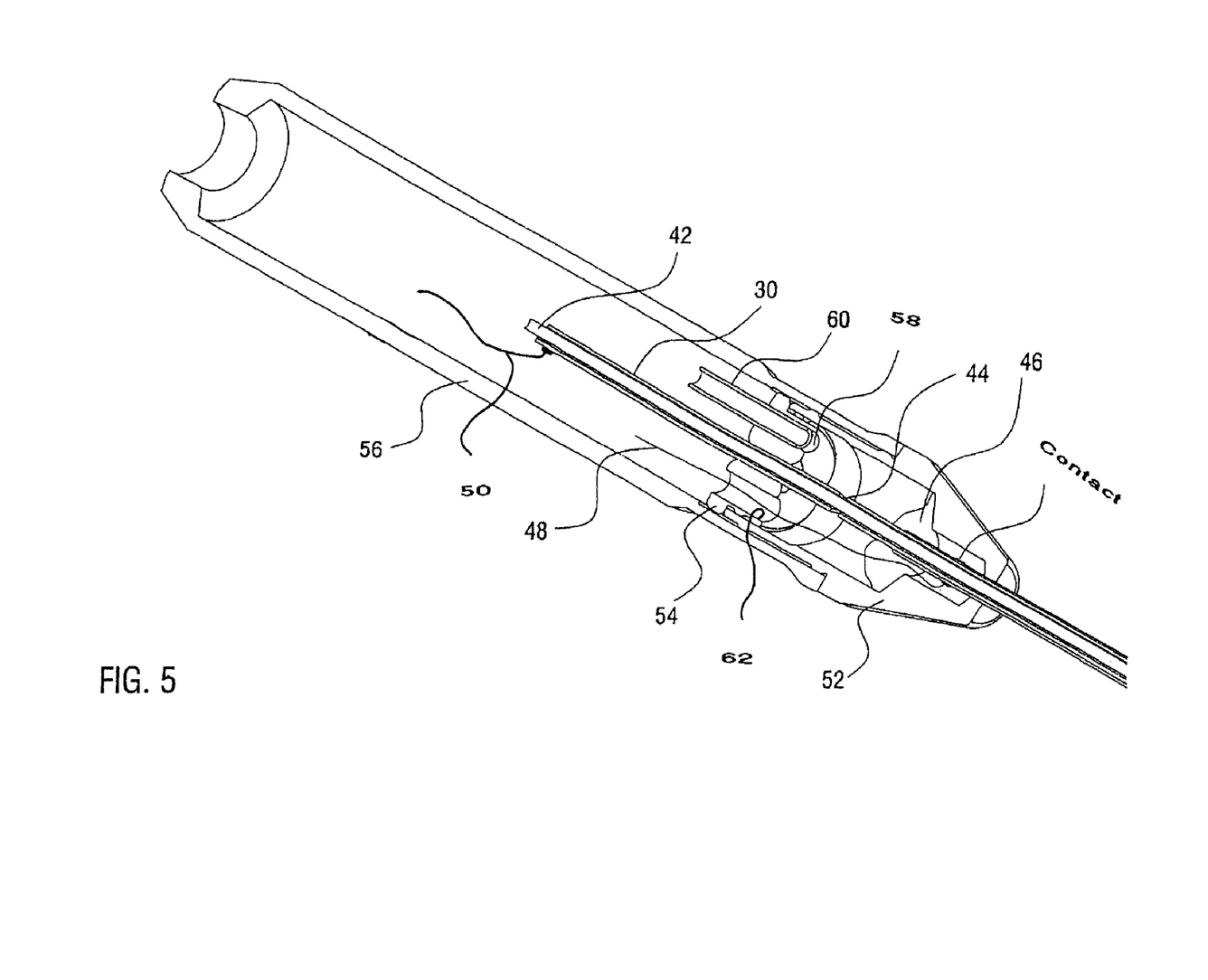
FIG. 5 is a view in longitudinal section on an enlarged scale showing the proximal end of the surgical probe of FIGS. 1 and 2.

The view in FIG. 5 in longitudinal section, on an enlarged scale in relation to FIG. 2, shows the handle 14 in longitudinal section together with the proximal end of the shaft 12.

In regard to the shaft 12 it is worth noting that the metal tube 40 extends proximally into the handle 14 further than the outer insulating layer. In addition the inner insulating layer 36 extends into the interior of the handle 14 further than the metal tube 40. The hollow body 30 even extends into the interior of the handle 14 considerably further than the inner insulating layer 36 and on the other side of the proximal end of the inner insulating layer 36 has a transverse bore 44, through which liquid can issue outwardly from the cavity forming the fluid passage 26 in the interior of the hollow body 30.

Finally the plastic hose 42 projects proximally out of the fluid passage 26 so that the plastic hose 42 can be connected for example to a pump for a cooling fluid. The cooling fluid is best conveyed by the pump to the distal end of the plastic hose 42, there issues from a mouth opening of the plastic hose 42 and flows between the outside wall of the plastic hose 42 and the inside wall of the fluid passage 26 back into the handle 40 in order there to issue from the fluid passage 26 by way of the transverse bore 44.

At the location where the outer insulating layer 22 and the metal tube 40 proximally terminate, the shaft 12 is enclosed by an electrically insulating sealing material 46. The proximal end of the metal tube 40 is electrically contacted within the insulating sealing material 40 so that it is to be connected by means of a cable 48 to one pole of a generator for a high-frequency voltage.

The proximal end of the hollow body 30 is electrically connected to a second cable 50, by means of which an electrical connection is to be made to a second pole of a generator for high-frequency voltage.

In regard to the structure of the handle 14 it can be seen from FIG. 5 that a distal end portion 52 of the handle 14 forms a first sub-holding means for the shaft 12. A proximal holding portion 54 is inserted in an opening at the proximal end of the distal end 52 and forms a second holding means for the shaft 12. The unit comprising the distal end portion 52 and the proximal holding means 54 is pushed into a distal opening of a hand portion 56.

The distal end portion 52 and the proximal holding means 54 enclose the cavity 24. The transverse bore 44 is also arranged in that cavity 24 in the hollow body 30 so that cooling fluid issuing from the fluid passage 26 flows into the cavity 24 and can flow away by way of a conduit 60 inserted into a through bore 58 in the proximal holding means 54. A second through bore 62 in the proximal holding means 54 serves as a ducting means for the cable 48 and is moreover sealed off with sealing material.

The invention claimed is:

1. A surgical probe, comprising:
a handle and a shaft which is connected to the handle;
wherein the shaft comprises:
a proximal electrode;
a distal electrode; wherein the proximal electrode is nearer to the handle than the distal electrode,
an insulator; and
a hollow body extending from the handle, the distal end of the hollow body integrally forming the distal electrode, with the hollow body being distally closed, made of metal and electrically conductive;
wherein the hollow body comprises a portion of smaller outside diameter and a portion of larger outside diameter, wherein the portion of larger outside diameter comprises the distal electrode and wherein the portion of smaller outside diameter is externally enclosed by and supports the proximal electrode and the insulator thereon, wherein the insulator electrically insulates the proximal electrode from the enclosed distal electrode, with the insulator comprising an insulating layer supported on the hollow body and positioned in a radial direction between the hollow body and the enclosing proximal electrode; the hollow body of the distal electrode further comprising a fluid passage in the interior thereof, configured for passage of a cooling fluid therein;
wherein the proximal and distal electrodes comprise an outer surface of the shaft and are axially separated from each other by the insulator;
wherein the outside diameter of the two electrodes and the outside diameter of the insulator are approximately equal;
and wherein the probe is configured to have a mechanical strength, rigidity and perforation capability that permits insertion of the shaft into body tissue.

2. A surgical probe as set forth in claim 1, wherein the insulating layer of the insulator is arranged between the hollow body and the proximal electrode and at the interface between the hollow body and the insulator.

3. A surgical probe as set forth in claim 1, wherein the insulating layer is formed by shrink tube.

4. A surgical probe as set forth in claim 1, wherein the proximal electrode is formed by a metal tube of a diameter which is substantially equal over its length and of substantially equal wall thickness.

5. A surgical probe as set forth in claim 1, wherein the fluid passage extends in the hollow body to the closed end thereof and is of a diameter which is substantially equal throughout.

6. A surgical probe as set forth in claim 1, wherein the hollow body is shaped to a point at its distal end.

7. A surgical probe as set forth in claim 1, wherein in the region of the distal electrode the hollow body is of an outside diameter which is approximately equal to the outside diameter of the proximal electrode or of the insulator.

8. A surgical probe as set forth in claim 1, wherein a hose is in the interior of the fluid passage, with a mouth of the hose opening in the proximity of the closed distal end of the fluid passage, which hose is so arranged and connected that a cooling fluid is to be passed through the hose into the proximity of the distal end of the fluid passage, there issues from the mouth opening of the hose and can flow back between the hose and the wall of the fluid passage to the proximal end of the shaft.

9. A surgical probe as set forth in claim 1, wherein at its proximal end the shaft is connected to the handle and is there partially embedded in sealing material in such a way that the tube forming the proximal electrode is completely embedded at its proximal end in the sealing material while the proximal end of the hollow body projects from the sealing material.

10. A surgical probe as set forth in claim 9, wherein the proximal electrode is electrically contacted within the sealing material.

* * * * *